United States Patent
Farley

(10) Patent No.: US 6,544,564 B1
(45) Date of Patent: Apr. 8, 2003

(54) CYTOTOXIC PHARMACEUTICAL COMPOSITION

(76) Inventor: Michael Donald Farley, 225 5th Ave., Suite 6, Indialantic, FL (US) 32903

( * ) Notice: Subject to any disclaimer, the term of this patent is extended or adjusted under 35 U.S.C. 154(b) by 0 days.

(21) Appl. No.: 09/995,173

(22) Filed: Nov. 27, 2001

(51) Int. Cl.$^7$ ............................................. A61K 35/78
(52) U.S. Cl. .................. 424/729; 424/451; 424/195.15; 424/756; 514/2
(58) Field of Search ........................... 424/451, 195.15, 424/756, 729; 514/2

(56) References Cited

U.S. PATENT DOCUMENTS

| | | | |
|---|---|---|---|
| 5,416,070 A | * | 5/1995 | Vosika et al. |
| 5,824,648 A | * | 10/1998 | Yang et al. |
| 5,904,924 A | * | 5/1999 | Gaynor et al. |
| 5,910,308 A | * | 6/1999 | D'Jang |
| 5,935,581 A | * | 8/1999 | Kapadia et al. |
| 5,948,808 A | * | 9/1999 | Safe |
| 6,008,260 A | * | 12/1999 | Pezzuto et al. |

OTHER PUBLICATIONS

Choi et al. Anticancer Research (1999), vol. 19, pp. 5229–5233.*
Ong et al. Gen. Pharmacol. (1997), vol. 29, No. 2, pp. 121–126.*

* cited by examiner

Primary Examiner—Leon B. Lankford, Jr.
Assistant Examiner—Susan D. Coe

(57) ABSTRACT

An inventive and proprietary formula to enhance the body's natural immune function against viral and infectious diseases and cancer. The composition per unit dose in liquid or capsule gel caplets consists of:

200 to 600 mg. of Chrysin;
  200 to 600 mg. of Colorius Versicolor PSK;
  50 to 150 mg. of 3,3' Diindolylmethane DIM;
  50 to 150 mg. of Resveratrol 25%;
  50 to 150 mg. Turmeric Extract 95%;
  40 to 140 mg. Green Tea Extract 95%;
  20 to 80 mg. of Quercitin Dihydrate 99%; and
  15 to 75 mg. of Phosphatidyl Choline 50%

Advantageously, each dose unit preferably includes 25 mg. to about 150 mgs. of Myricetin.

6 Claims, No Drawings

CYTOTOXIC PHARMACEUTICAL COMPOSITION

This invention relates to an immunity system of a human body, against viral and infectious disease and cancer.

The immune function is a system that functions to include absorption of excess fluid and its return to the blood stream, absorption of fat and finally to the immune system function.

Immunity is the body's capability to repel foreign substances and cells. The non specific responses are the first line of defense. Highly specific responses are the second line of defenses and are tailored to an individual threat.

Accordingly to the present invention, a pharmaceutical composition per unit dose in liquid or capsule gel caplets, characterized in that each dose unit in compound form consists of:
- (a) 200 to 600 mg. of Chrysin
- (b) 200 to 600 mg. of Colorius Versicolor (PSK)
- (c) 50 to 150 mg. of 3,3' Diindolymethan (DIM)
- (d) 50 to 150 mg. of Resveratrol 25%
- (e) 50 to 150 mg. of Turmeric Extract 95%
- (f) 40 to 140 mg. of Green Tea Extract 95%
- (g) 20 to 80 mg. of Quercitin Dihydrate 99%
- (h) 15 to 75 mg. of Phosphtidyl Choline 50%

Preferably the invention may also include 25 mg. to about 150 mg. of Myricetin.

The present invention, advantageously may include a pharmaceutical composition per unit dose in liquid or capsule gel caplets characterized in that each dose per unit in compound form consists of:
- (a) 200 to 600 mg. Chrysin
- (b) 200 to 600 mg. Colorius Versicolor (PSK)
- (c) 50 to 150 mg. 3,3' Diindolymetane (DIM)
- (d) 50 to 150 mg. Resveratrol 25%
- (e) 50 to 150 mg. Turmeric Extract 95%
- (f) 40 to 140 mg. Green Tea Extract 95%
- (g) 20 to 80 mg. Quercitin Dihydrate 99%
- (h) 15 to 75 mg. Phosphtidyl Choline 50%
- (i) 25 mg to about 150 mg. of Myricetin These all natural formulas contain phytochemicals that have been shown to cause cell apoptosis, cytotoxicity and inhibition of replication in all of the following cancer cell lines.
TBP-1 human monocytic leukaemia cells
CaCo-2 human colon cancer cells
Human leukaemia HL-60 cells
HLA B40-positive breast cancer cells
Estrogen receptor positive MCF-7 (human breast cancer cell lines)
Estrogen receptor negative MDA-MB-468 (human breast cancer cell lines)
Squamous cell carcinoma (SCC) (oral)
Androgen-sensitive LNCaP (human prostate)
Androgen-insensitive PC-3 cell lines (human prostate)

These phytochemicals have also been tested and found to be effective against the HIV and Herpes viruses. It functions on two levels. On one level it acts directly and positively on the immune system. It does this by increasing the number and function of the body's own natural killer cells as well as by increasing the number and function of lymphocytes. For this reason, it may be one of the most effective prophylactics agains cancer and viral infections available on the market.

The phytochemicals are suspended in liposome's to enhance bioavailability. This same technology is currently being used to enhance the efficacy of some chemotherapeutic agents. It offers a much more direct presentation of the desired phytochemicals to the lymphatic system.

However, the present invention plays a totally new role to stabilize and form within a body's natural immune function system an enhanced defense mechanism against viral infectious disease and cancer.

The composition per unit dose in liquid form is given as a normal dosage of two tablespoons three times daily. The dose per unit besides being in liquid form, may also be converted into capsule gel caplets, making it easier to give to a patient, in lie of the liquid dosage.

An inventive and proprietary formula to enhance the body's natural immune function against viral and infectious diseases and cancer. The composition per unit dose in liquid or capsule gel caplets consists of.
- (a) 200 to 600 mg. of Chrysin
- (b) 200 to 600 mg. of Colorius Versicolor (PSK)
- (c) 50 to 150 mg. of 3,3 Diindolymethane (DIM)
- (d) 50 to 150 mg. of Resveratrol 25%
- (e) 50 to 150 mg. of Turmeric Extract 95%
- (f) 40 to 140 mg of Green Tea Extract 95%
- (g) 20 to 80 mg. of Quercitin Dihydrate 99%
- (h) 15 to 75 mg. of Phosphtidyl Choline 50%

Advantageously, each dose unit preferably includes 25 mg. to about 150 mg. of Myricetin.

What is claimed is:

1. A pharmaceutical composition per unit dose in liquid form or capsule gel caplet characterized in that each unit dose form consists of:
   200 to 600 mg. of Chrysin;
   200 to 600 mg. of Coriolus Versicolor PSK;
   50 to 150 mg. of 3,3' Diindolylmethane Dim;
   50 to 150 mg. of Resveratrol 25%;
   50 to 150 mg. Turmeric Extract 95%;
   40 to 140 mg. of Green Tea Extract 95%;
   20 to 80 mg. of Quercitin Dihydrate 99%; and
   15 to 75 mg. of Phosphatidyl Choline 50%.

2. A pharmaceutical composition per unit dose as claimed in claim 1, characterized in that each dose also includes 25 mg. to about 150 mgs. of Myricetin.

3. A pharmaceutical composition per unit dose in liquid form or capsule gel caplets as claimed in claim 1, characterized in that the amount in per unit dose form consists of:
   400 mg. Chrysin;
   400 mg. Coriolus Versicolor PSK;
   100 mg. 3,3' Diindolylmethane DIM;
   100 mg. Resveratrol 25%
   100 mg. Turmeric Extract 95%;
   90 mg. Green Tea Extract 95%;
   50 mg. Quercitin Dihydrate 99%; and
   40 mg. Phosphatidyl Choline 50%.

4. A pharmaceutical composition per unit dose in liquid or capsule gel caplets as claimed in claim 2, characterized in that the amount in per unit dose form consists of:
   400 mg. Chrysin;
   400 mg. Coriolus Versicolor PSK;
   100 mg. 3,3' Diindolylmethane DIM;
   100 mg. Resveratrol 25%;
   100 mg. Turmeric Extract 95%;
   90 mg. Green Tea Extract 95%;

50 mg. Quercitin Dihydrate 99%;
40 mg. Phosphatidyl Choline 50%; and
100 mg. Myricetin.

5. A pharmaceutical composition per unit dose in liquid or capsule gel caplets characterized in that each dose per unit in compound form consists of:
200 to 600 mg. Chrysin;
200 to 600 mg. Coriolus Versicolor PSK;
50 to 150 mg. 3,3' Diindolylmethane DIM;
50 to 150 mg. Resveratrol 25%;
50 to 150 mg. Turmeric Extract 95%;
40 to 140 mg. Green Tea Extract 95%;
20 to 80 mg. Quercitin Dihydrate 99%;
15 to 75 mg. Phosphatidyl Choline 50%; and
25 mg. to about 150 mg. of Myricetin.

6. A pharmaceutical composition per unit dose in liquid or capsule gel caplets characterized in that each dose per unit in compound form consists of:
400 mg. Chrysin;
400 mg. Coriolus Versicolor PSK;
100 mg. 3,3' Diindolylmethane DIM;
100 mg. Resveratrol 25%;
100 mg. Turmeric Extract 95%;
90 mg. Green Tea Extract 95%;
50 mg. Quercitin Dihydrate 99%;
40 mg. Phosphatidyl Choline 50%; and
100 mg. Myricetin.

* * * * *